United States Patent [19]

Nakanishi

[11] 4,433,957
[45] Feb. 28, 1984

[54] TRANSMISSION GEAR FOR A DENTAL HANDPIECE

[75] Inventor: Toshimasa Nakanishi, Kanuma, Japan

[73] Assignee: Nakanishi Dental Mfg. Co., Ltd., Kanuma, Japan

[21] Appl. No.: 351,313

[22] Filed: Feb. 22, 1982

[51] Int. Cl.³ .............................................. A61C 1/02
[52] U.S. Cl. ..................................... 433/105; 433/126
[58] Field of Search ................................ 433/105, 126

[56] References Cited

U.S. PATENT DOCUMENTS 3,436,980  4/1969  Loge et al. .......................... 433/105

FOREIGN PATENT DOCUMENTS 604992  11/1934  Fed. Rep. of Germany ...... 433/105
53-129492 11/1978  Japan .................................. 433/105

Primary Examiner—Robert Peshock
Attorney, Agent, or Firm—Wenderoth, Lind & Ponack

[57] ABSTRACT

The present transmission gear for a dental handpiece generally has a handle portion including a biased guide slot and a holding sleeve fixedly held in the handle portion, a first cylindrical hollow driven shaft, a second driven shaft having at its rear end portion an axial central cavity and fixedly inserted into the first driven shaft, a shiftable clutch shaft having a drive pin, a collar bearing including a slidable pin and a crossed male lug and journaled rotatably in the central hollow, a planetary gear train provided at the rear end portion of the clutch shaft, and a drive gear coupled to the motor to be engaged with the clutch shaft whereby the clutch shaft is either coupled to the drive shaft or disengaged therefrom by the alternative rotation of an operating ring to deliver either a direct transmission of the motor rotation or reduced speed rotation thereof to a dental tool.

3 Claims, 6 Drawing Figures

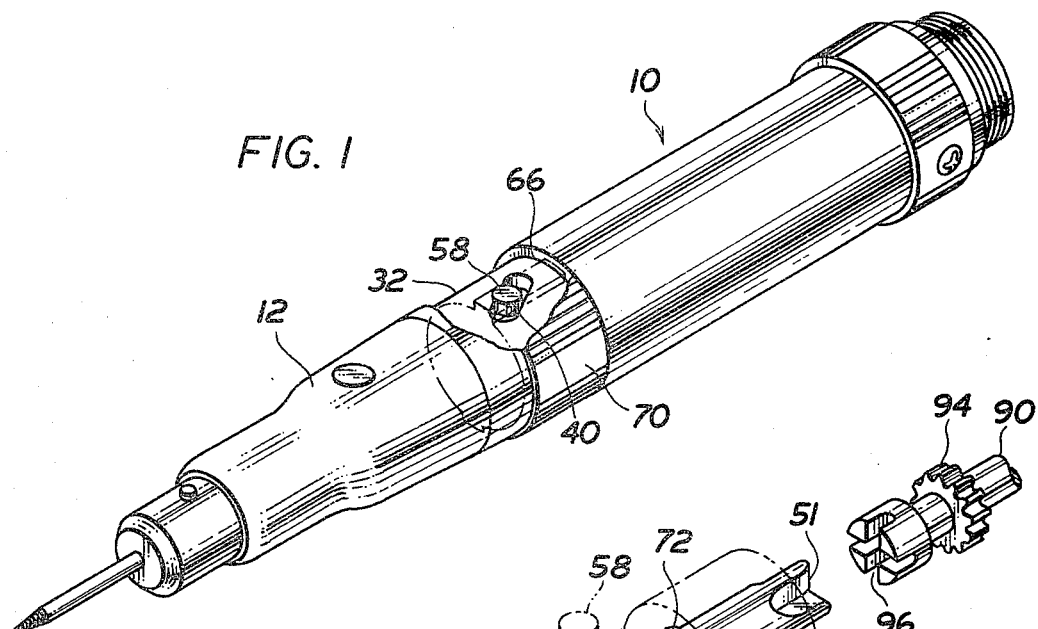
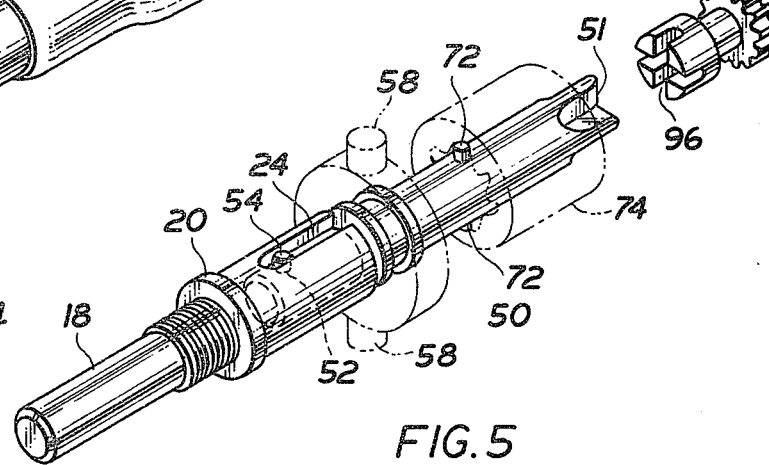
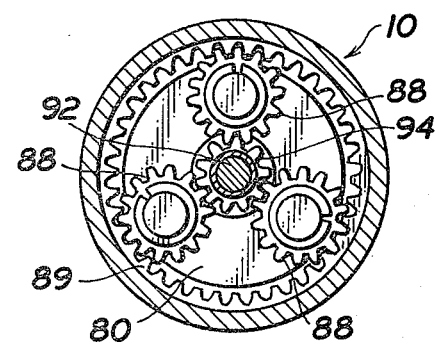
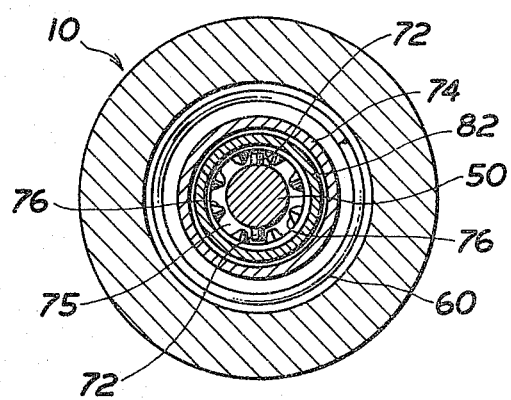

TRANSMISSION GEAR FOR A DENTAL HANDPIECE

BACKGROUND OF THE INVENTION

This invention relates to improvements in a dental handpiece, and more particularly to a transmission gear for a dental handpiece.

In the conventional transmission gear for a dental handpiece such as disclosed in the specification of the Japanese Patent Application Publication (not-examined) No. 129,492/1978, coupling members 16 and 17 are provided in both the axial and radial directions from a drive shaft 6, and these coupling members are not coupled to a driven shaft, but are selectively engageable with coupled members 18 or 19 of a driven sleeve 10.

It has been found, however, that it is not only difficult to make such a complicated device, but the selective engagement of these coupling members 16 and 17 with the coupled members 18 and 19 can not be carried out easily. In addition, the delivery of torque is carried out through the medium of these coupling and coupled members so that these members are worn out easily, resulting in inaccurate delivery of torque.

A principal object of this invention is to provide a transmission gear for a dental handpiece which includes a shiftable clutch shaft interposed between a drive shaft and a driven shaft, a collar bearing provided respectively at a middle portion and a planetary gear train at the rear end of the clutch, shaft whereby the torque of a driving motor can be properly delivered to the driven shaft.

Another object of this invention is to provide a transmission gear for a dental handpiece including an operating ring whereby a clutch shaft can be easily and rapidly shifted by a selective rotation of the operating ring to drive a dental tool at given speed.

Another object of this invention is to provide a transmission gear for a dental handpiece including no means of power delivery which will cause abrasion of the coupling and coupled members to ensure smooth rotation for a dental tool.

Still another object of this invention is to provide a dental handpiece which is comparatively simple and small, light in weight and at the same time desirably rigid, strong and durable.

BRIEF DESCRIPTION OF DRAWINGS

The above and further objects and novel features of the invention will more fully appear from the following detailed description when the same is read in connection with the accompanying drawings. It is to be expressly understood, however, that the drawings are for purpose of illustration only and not intended as a definition of the limits of the invention.

FIG. 1 is a partially cut away perspective view of a preferred embodiment of a dental handpiece according to the invention;

FIG. 4 is an enlarged perspective schematic view of a clutch shaft provided with a collar bearing, particularly showing coupling and disengaging relations with a drive shaft;

FIG. 5 is an enlarged transverse sectional view on line V—V of FIG. 2; and

FIG. 6 is an enlarged transverse sectional view on line VI—VI of FIG. 3.

DETAILED DESCRIPTION

Figure 2:
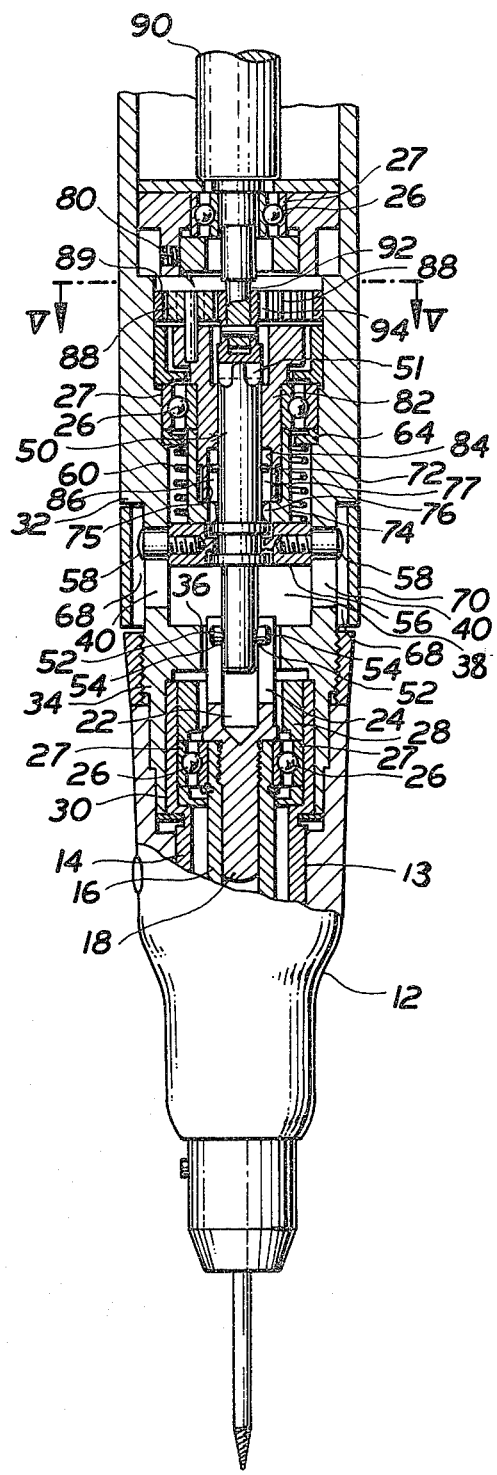
FIG. 2 is a greatly enlarged front view, partly in cross section, to show the internal construction of the dental handpiece shown in FIG. 1, illustrating a transmission gear coupled with a drive gear.
Figure 3:
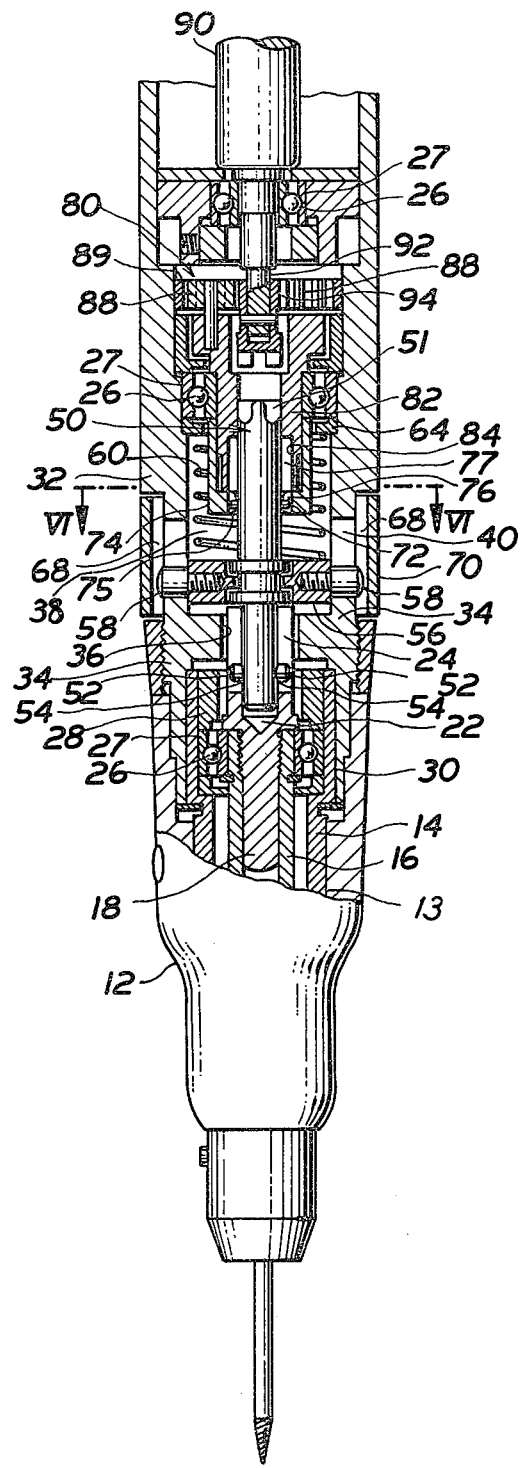
FIG. 3 is a view similar to FIG. 2 illustrating the transmission gear disengaged from the drive gear and coupled with a driven gear.

Referring to FIGS. 1, 2 and 3, a preferred embodiment which has been selected to illustrate this invention comprises a dental handpiece 10 including a handle portion 12 and a holding sleeve 14 fixedly held in the handle portion. A plurality of successively smaller cylindrical internal steps 13 are provided around the internal periphery of the handle portion 12 in the forward direction of the handle portion.

A first cylindrical hollow driven shaft 16 is rotatably journaled in the holding sleeve 14 by means of roller bearings 26 held in a bearing race 27.

A second driven shaft 18 is provided with a disc flange 20 and its middle portion and has a hollow axial cylindrical portion 22 extending partially into the shaft 18 from its rear end, and a longitudinal diametrical slot 24 is formed in this part of the shaft.

The bearing retainer 27 is held by a retaining ring 28 fixedly inserted into a recess in the holding sleeve 14.

A front male portion 30 of the dental handpiece 10 is provided with a successively smaller cylindrical steps fitting onto the cylindrical internal steps 13 of the handle portion 12 to allow insertion of the male portion and intimate contact of the steps. A central axial opening 36 is formed through a rear partition wall 34 of the handpiece 10.

The second driven shaft 18 is inserted into the hollow cylindrical portion 22 of the first driven shaft 16.

A spiral guide slot 40 is provided in the handpiece 10 on opposite sides of a central hollow portion 38 thereof.

A cotter or drive pin 54 extends through a diametrical opening 52 near a front portion of a clutch shaft 50, and a collar bearing 56 having a pair of pins 58 at diametrically opposite portions is rotatably mounted at a middle portion of the clutch shaft, with the pins 58 in the slot 40 for causing the collar bearing 56 to move in the axial direction of the clutch shaft 50 while rotating slightly.

The front male portion of the dental handpiece 10 is fixedly inserted from the rear into the cylindrical interior of the handle portion 12 and a coil spring 60 is interposed in a cylindrical hollow 62 defined between an inner peripheral wall of the middle portion 32 and an outer peripheral wall of a first sleeve 74 with the ends of the coil spring 60 against the collar bearing 56 and a washer 64 held in a recess in the cylindrical hollow 62. The washer 64 is in turn supported by a further bearing race 27.

A recess 66 is provided at a peripheral end portion of the dental handpiece 10 into which the spiral guide slots 40 open so that the outer ends of the pins 58 can be engaged to hold the coil spring 60 in its compressed state.

A rotatable operating ring 70 is mounted in the peripheral recess 66 defined around the middle portion 32 of the dental handpiece 10 and has a longitudinally extending slots 68 on the inner periphery thereof in which the outer ends of pins 58 are engaged.

Provided at a rear end portion of the clutch shaft 50 is a crossed male lug 51, which is coupled with a crossed slot 96 provided at a front end portion of a drive shaft 92 of a motor 90. As shown in FIGS. 2 and 3, the drive shaft 92 is journaled in bearings 24 held in a cylindrical hollow 94.

A pair of lugs 72 diametrically protrude from an intermediate portion of shaft 50 between the collar bearing 56 and a rear end portion of the clutch shaft 50. The crossed male lug 51 and the crossed slot 96 are chamfered so as to facilitate an easy coupling with each other.

The first sleeve 74 having a small internal hollow 75 and a large internal hollow 77 is fitted onto the clutch shaft 50. A corrugated guide 76 is provided around the inner periphery of the small internal hollow 75.

A second sleeve 82 having at its front orifice an outer periphery 84 to fit into the large internal hollow 77, an internal hollow 86 to receive the two lugs 72, and three planet gears 88 each provided at equal intervals around the periphery of the rear end thereof is fitted onto the clutch shaft 50. A central gear 94 provided on the front end of the drive gear 92 is in mesh with the three planet gears 88 which, in turn, are engaged with an internal gear 89 to form a planetary gear train 80.

In operation by rotating the operating ring 70 in one direction with the fingers, the outer ends of the slidable pins 58 are moved along the guide slots 40 by engagement in grooves 68 (as shown in FIG. 2) so that the collar bearing 56 urges the coil spring 60 to shift the clutch shaft 50 to its rearmost position.

At this time, the crossed male lug 51 is inserted into the crossed slot 96 at the front end portion of the drive shaft 92, and in this case the force of the coil spring 60 is maintained by the engagement of the head of the slidable pin 58 within the dent 66.

Accordingly, the rotation of the motor 90 is transferred directly to the clutch shaft 50 with a gear-reduction ratio of 1:1 in order to rotate the driven shaft 16 by means of the drive pin 54 and the driven shaft 18.

On the other hand, when the ring 70 is rotated into its opposite extreme position as shown in FIG. 3, the coil spring 60 is allowed to elongate by the reverse motion of the slidable pin 58 and to shift the clutch shaft 50 to its extreme front position (as shown in FIG. 3), thus bringing the top end portion of the clutch shaft 50 into the cavity at the rear end of the driven shaft 18. At the same time, the crossed male lug 51 of the clutch shaft 50 is disengaged from the crossed slot 96 of the drive gear 92 to engage the lugs 72 in the corrugated guide 76 of the first sleeve 74 of the planetary gear train 80. In this state, the velocity of rotation of the motor 90 is changed in accordance with the gear-reduction ratio (for instance 3:1) among the planet gears 88 and the central gear 94 so that the clutch shaft 50 is driven at a reduced speed, thus rotating the driven shaft 16 slowly correspondingly.

From the foregoing, it is believed that the features and advantages of my invention will be readily apparent to those skilled in the art and it will be understood that changes in the form, proportion and minor details of construction may be resorted to without departing from the spirit or the scope of the appended claims.

I claim:

1. A dental handpiece having a two speed transmission, comprising:
   a hollow handle means;
   a holding sleeve fixedly held in said handle means;
   cylindrical driven shaft means rotatably journalled in said holding sleeve and having a hollow axial cylindrical recess at the rear end and having a diametrical longitudinal slot therethrough;
   said handle means having a peripheral recess around the outside of said handle means at the middle portion thereof and at least one spirally extending guide slot therein opening into the interior of said handle means;
   a clutch shaft in the interior of said handle means and axially movable therein, said clutch shaft having a cotter at the forward end extending diametrically through said slidable in said slot in said driven shaft means;
   a collar having a radially extending pin thereon and rotatably mounted on said clutch shaft at a middle portion thereof and fixed against axial movement along said clutch shaft and having said pin extending through said spiral slot, said clutch shaft further having first engagement means at the rear end thereof;
   a coil spring in said interior of said handle means engaged with said collar urging said collar toward said driven shaft means; a sleeve means rotatably mounted in a fixed position in the interior of said handle means coaxial with said clutch shaft, said clutch shaft having second engagement means engagable with said sleeve for causing rotation of said clutch shaft with said sleeve means when said clutch shaft is in a forward position and disengaged from said sleeve means when said clutch shaft is in a rearward position;
   planet gear means mounted on the rear end of said sleeve means;
   a central gear within said planet gear means and engaged therewith;
   a motor means on which said central gear is mounted, said central gear having a third engagement means thereon engagable with said first engagement means when said gear shaft is in the rearward position; and an operating ring around the handle means in said recess and engagable with said pin for, when said operating ring is rotated, moving said pin along said spiral groove to move said clutch shaft between the forward and rearward positions.

2. A dental handpiece as claimed in claim 1 wherein said first engagement means is a male lug having a cross-shape and said third engagement means is a cross-shaped recess, and said male lug and said recess are chamfered to allow an easy coupling with each other.

3. A dental handpiece as claimed in claim 1 wherein said collar comprises a collar member fixed to said clutch shaft, a collar bearing rotatable around said collar member and having said pins thereon, and said operating ring has a longitudinally extending groove in the inner periphery in which said pin is engaged.

* * * * *